United States Patent [19]

Ishiguro et al.

[11] Patent Number: 5,340,718
[45] Date of Patent: Aug. 23, 1994

[54] METHOD FOR ASSAYING A HUMAN MUSCULAR DYSTROPHY PROTEIN

[75] Inventors: Tsuneo Ishiguro; Chikahiko Eguchi, both of Kawasaki, Japan

[73] Assignee: Ajinomoto Co., Inc., Tokyo, Japan

[21] Appl. No.: 9,392

[22] Filed: Jan. 27, 1993

Related U.S. Application Data

[63] Continuation of Ser. No. 318,952, Mar. 6, 1989, abandoned.

[30] Foreign Application Priority Data

Mar. 4, 1988 [JP] Japan .................................. 63-51313
Sep. 21, 1988 [JP] Japan ................................. 63-237200

[51] Int. Cl.$^5$ ...................... G01N 33/53; C07K 7/10; C07K 15/00; C07K 15/28
[52] U.S. Cl. ...................... 435/71; 530/324; 530/387.9; 530/389.1; 530/388.85
[58] Field of Search ............ 435/7.1; 530/324, 388.85, 530/387.9, 389.1

[56] References Cited

U.S. PATENT DOCUMENTS 5,239,060 8/1993 Kunkel et al. .................... 530/350

OTHER PUBLICATIONS

Goodman, J. W., "Immunogenicity & Antigenic Specificity," in *Basic & Clinical Immunology* (ed. Stites et al.) pp. 20-21 (1987).

Arahata et al., Nature 337, 606 (1989).
Shimizu, et al. "A Monoclonal Anbtibody Against a Synthetic Polypeptide Fragment of Dystrophin (AA Seq. 215-264)," Proc. Jpn. Acad. 64:205-8 (1988).
Zubrzycka-Gaarn et al. "The Duchenne muscular dystrophy gene product is localized in sarcolemma of human skeletal muscle," Nature 333:466-469.
Kao et al. "Immunological identification of a high molecular weight protein as a candidate for the product of the Duchenne muscular dystrophy gene," Proc. Neur Acad Sci 85:4491-95 (1988).
Koenig et al., Complete cloning of the Duchenne Muscular Dystrophy (DMD) cDNA and preliminary genomic organization of the DMD gene in normal and affected individuals, Cell 50, 509-517 (1987).
Hoffman et al., Dystrophin: The protein product of the Duchenne muscular dystrophy locus, Cell 51, 919-928 (1987).
E. P. Hoffman et al: Science, 238, 347 (1987).
E. P. Hoffmann et al: Nature, 330, 754 (1987).
K. Arahata et al: Nature, 333, 861 (1988).

*Primary Examiner*—Christine M. Nucker
*Assistant Examiner*—M. P. Woodward
*Attorney, Agent, or Firm*—Oblon, Spivak, McClelland, Maier & Neustadt

[57] ABSTRACT

Methods and polypeptides for assaying human proteins associated with Duchenne muscular dystrophy, are disclosed.

8 Claims, 1 Drawing Sheet

FIG.1
FIG.2
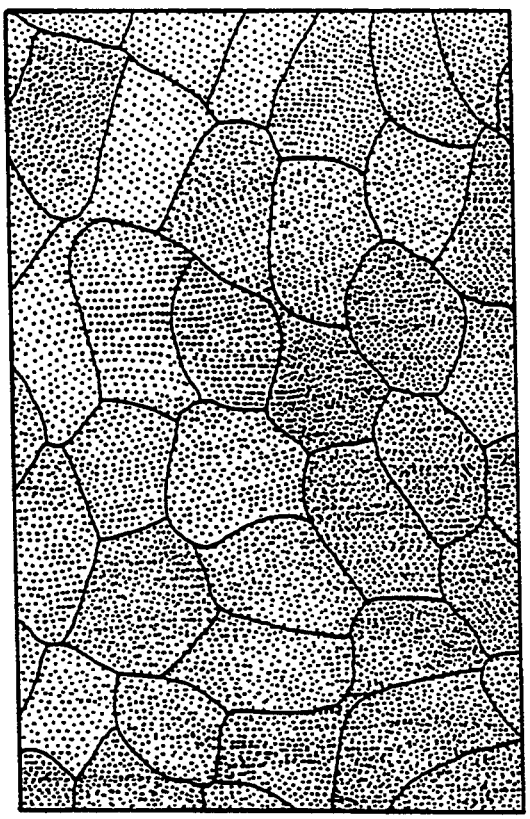
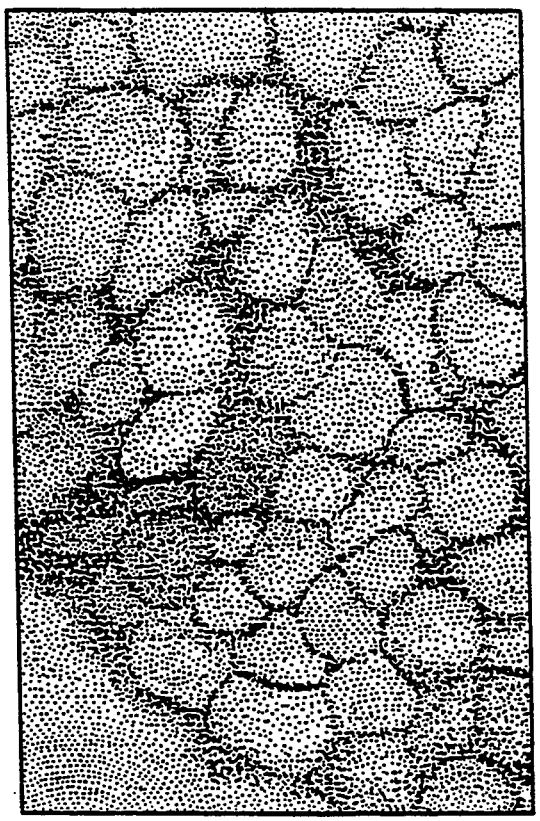

METHOD FOR ASSAYING A HUMAN MUSCULAR DYSTROPHY PROTEIN

This application is a continuation of application Ser. No. 07/318,952, filed on Mar. 6, 1989, now abandoned.

BACKGROUND OF THE INVENTION

1. Field of the Invention

The present invention relates to a method for assaying dystrophin which is a protein defective in a human suffering from Duchenne muscular dystrophy (DMD) which is a hereditary disease.

2. Discussion of the Background

Duchenne muscular dystrophy is a hereditary disease which is developed almost only in males. A gene which is defective peculiarly to this disease is located on the X chromosome and its sequence has been elucidated [M. König, E. P. Hoffman, C. J. Bertelson, A. P. Monaco, C. Feenet and L. M. Kunkel: Cell, 50, 509 (1987), E. P. Hoffman, A. P. Monaco, C. C. Feeher and L. M. Kunkel, Science, 238, 347 (1987)]. If any antibody capable of specifically recognizing dystrophin which is a protein encoded by this gene is produced, a deletion or defect of dystrophin specific to this disease could be detected and such would be useful. A related method was tried by Hoffman et al., using the gene from mice suffering from a disease which is the same type as Duchenne muscular dystrophy [E. P. Hoffman, R. H. Brown, Jr. and L. M. Kunkel, Cell, 51, 919 (1987); E. P. Hoffman, C. M. Knudson, K. P. Campbell and L. M. Kunkel, Nature, 330, 754 (1987)]. However, the method of Hoffman et al. uses a gene from mice, the amino acid sequence of which is different by about 10% from that of humans, to produce the antibody so that it is inappropriate to determine dystrophin possessed by humans. Moreover, according to this method, protein having a high molecular weight such as 208 amino acid residues or 410 amino acid residues is used as an antigen and hence, the method has a shortcoming that an antibody capable of reacting not only with dystrophin but also with many other proteins is formed and that the antibody fails to specifically react with dystrophin alone. In order to compensate for the poor specificity of reaction, Hoffman et al. adopted a method using a specimen obtained by previously homogenizing cells to be tested followed by separating protein from the homogenate by electrophoresis, and then performing an antigen-antibody reaction with respect to the specimen. For this reason, the method encounters a drawback that operations are complicated and is thus unsatisfactory.

In general, conventional methods for assaying dystrophin have drawbacks in that antibodies capable of specifically reacting only with dystrophin could not be obtained since a gene from a mouse, which is different from that of a human, has been used for preparation of the antibody. Further, operations are complicated since the method comprises using a specimen obtained by previously homogenizing cells to be tested and separating protein from the homogenate by electrophoresis and performing an antigen-antibody reaction with respect to the specimen. Therefore, the present inventors have made extensive investigations to discover a method for assaying the protein in cells in a simple manner, by preparing an antiserum capable of specifically reacting only with dystrophin or an antibody fraction separated from the antiserum using a part of dystrophin encoded by human Duchenne muscular dystrophy-associated gene and performing an antigen-antibody reaction between a substance to be tested and the antiserum or antibody fraction.

SUMMARY OF THE INVENTION

In view of the foregoing problems, the present inventors have made extensive studies and as a result, have found a method for assaying dystrophin which is a protein defective in a human suffering from Duchenne muscular dystrophy, which comprises preparing a peptide containing all or a part of an amino acid sequence encoded by Duchenne muscular dystrophy gene or a derivative thereof, administering said peptide or a derivative thereof to a mammal to form antiserum in the mammal, obtaining the antiserum, and then reacting said antiserum or an antibody fraction separated from said antiserum with a substance to be tested and assaying the antigen-antibody complex formed.

In the method described above, the amino acid sequence encoded by gene is as follows:

```
1
MLWWEEYEDC    YEREDYQKKT    FTKWVNAQFS    KFGKQHIENL    FSDLQDGRRL
LDLLEGLTGQ    KLPKEKGSTR    VHALNNVNKA    LRYLQNNNYD    LYNIGSTDIY
DGNHKLTLGL    IWNIILHWQY    KNYMKNIMAG    LQQTNSEKIL    LSWVRQSTRN
YPQVNVINFT    TSWSDGLALN    ALIHSHRPDL    FDWNSVVCQQ    SATQRLEHAF
NIARYQLGIE    KLLDPEDVDT    TYPDKKSILM    YITSLFQVLP    QQVSIEAIQE
VEMLPRPPKV    TKEEHFQLHH    QMHYSQQITY    SLAQGYERTS    SPKPRFKSYA
YTQAAYVTTS    DPTRSPFPSQ    HLEAPEDKSF    GSSLMESEYN    LDRYQTALEE
VLSWLLSAED    TLQAQGEISN    DVEVVKDQFH    THEGYMMDLT    AHQGRVGNIL
QLGSKLIGTG    KLSEDEETEV    QEQMNLLNSR    WECLRVASME    KQSNLHRVLM
DLQNQKLKEL    NDWLTKTEER    TRKMEEEPLG    PDLEDLKRQV    QQHKVLQEDL
EQEQVRVNSL    THMVVVVDES    SGDHATAALE    EQLKVLGDRW    ANICRWTEDR
WVLLQDILLK    WQRLTEEQCL    FSAWLSEKED    AVNKIHTTGF    KDQNEMLSSL
QKLAYLKADL    EKKKQSMGKL    YSLKQDLLST    LKNKSVTQKT    EAWLDNFARC
WDNLVQKLEK    SIAQISQAVT    TTQPSLTQTT    VMETVTTVTT    REQILVKHAQ
EELPPPPPQK    KRQITVDSEI    RKRLDVDITE    LHSWITRSEA    VLQSPEFAIF
RKEGNFSDLK    EKYNAIEREK    AEKFRKLQDA    SRSAQALVEQ    MVMEGVNADS
IKQASEQLNS    RWIEFCQLLS    ERLNWLEYQN    NIIAFYNQLQ    QLEQMITTAE
NWLKIQPTTP    SEPTAIKSQL    KICKDEVNRL    SGLQPQIERL    KIQSIALKEK
GQGPMFLDAD    FVAFTNHFKQ    VFSDVQAREK    ELQTIFDTLP    PMRYQETMSA
IRTWVQQSET    KLSIPQLSVT    DYEIMEQRLG    ELQALQSSLQ    EQQSGLYYLS
TTVKEMSKKA    PSEISRKYQS    EFEEIEGRWK    KLSSQLYEHC    QKLEEQMNKL
RKIQNHIQTL    KKWMAEVDVF    LKEEWPALGD    SEILKKQLKQ    CRLLVSDIQT
IQPSLNSVNE    GGQKIKNEAE    PEFASRLETE    LKELNTQWDF    MCQQVYARKE
ALKGGLEKTV    SLQKDLSEMH    EWMTQAEEEY    LERDFEYKTF    DELQKAVEEM
KRAKEEAQQK    EAKVKLLTES    VNSYIAQAPP    VAQEALKKEL    ETLTTNYQWL
CTRLNGKCKT    LEEVWACWHE    LLSYLEKANK    WLNEVEFKLK    TTENIPGGAE
```

-continued

| | | | | |
|---|---|---|---|---|
| EISEVLDSLE | NLMRHSEDNP | NQIRILAQTL | TDGGVMDELI | NEELETFNSR |
| WRELHEEAVR | RQKLLEQSIQ | SAQETEKSLH | LIQESLITFID | KQLAAYOADK |
| VDAAQMPQEA | QKIQSDLTSH | EISLEEMKKH | NQGKEAAQRV | LSQIDVAQKK |
| LQDVSMKFRL | FQKPANFELR | LQESKMILDE | VKMHLPALET | KSVEQEVVQS |
| QLNHCVNLYK | SLSEVKSEVE | MVIKTGRQIV | QKKQTENPKE | LDERVTALKL |
| HYNELGAKVT | ERKQQLEKCL | KLSRKMRKEM | NVLTEWLAAT | DMELTKRSAV |
| EGMPSNLDSE | VAWGKATQKE | IEKQKVHLKS | ITEVGEALKT | VLGKKETLVE |
| DKLSLLNSNW | IAVTSRAEEW | LNLLLEYQKH | METFDQNYDH | ITKWIIQADT |
| LLDESEKKKP | QQKEDVLKRL | KAELNDIRPK | VDSTRDQAAN | LMANRGDHCR |
| KLVEPQISEL | NHRFAAISHR | IKTGKASIPL | KELEQFNSDI | QKLLEPLEAE |
| IQQGVNLKEE | DFNKDMNEDN | EGTVKELLQR | GDNLQQRITD | ERKREEIKIK |
| QQLLQTKHNA | LKDLRSQRRK | KALEISHQWY | QYKRQADDLL | KCLDDIEKKL |
| ASLPEPRDER | KIKEIDRELQ | KKKEELNAVR | RQAEGLSEDG | AAMAVEPTQI |
| QLSKRWREIE | SKFAQFRRLN | FAQIHTVREE | TMMVMTEDMP | LEISYVPSTY |
| LTEITHVSQA | LLEVEQLLNA | PDLCAKDFED | LFKQEESLKN | IKDSLQQSSG |
| RIDIIHSKKT | AALQSATPVE | RVKLQEALSQ | LDFQWEKVNK | MYKDRQGRFD |
| RSVEKWRRFH | YDIKIFNQWL | TEAEQFLRKT | QIPENWEHAK | YKWYLKELQD |
| GIGQRQTVVR | TLNATGEEII | QQSSKTDASI | LQEKLGSLNL | RWQEVCKQLS |
| DRKKRLEEQK | NILSEFQRDL | NEFVLWLEEA | DNIASIPLEP | GKEQQLKEKL |
| EQVKLLVEEL | PLRQGILKQL | NETGGPVLYS | APISPEEQDK | LENKLKQTNL |
| QWIKVSRALP | EKQGEIEAQI | KDLGQLEKKL | EDLEEQLNHL | LLWLSPIRNQ |
| LEIYNQPNQE | GPFDVQETEI | AVQAKQPDVE | EILSKGQHLY | KEKPATQPVK |
| RKLEDLSSEW | KAVNRLLQEL | RAKQPDLAPG | LTTIGASPTQ | TVTLVTQPVV |
| TKETAISKLE | MPSSLMLEVP | ALADFNRAWT | ELTDWLSLLD | QVIKSQRVMV |
| GDLEDINEMI | IKQKATMQDL | EQRRPQLEEL | ITAAQNLKNK | TSNQEARTII |
| TDRIERIQNQ | WDEVQEHLQN | RRQQLNEMLK | DSTQWLEAKE | EAEQYLGQAR |
| AKLESWKEGP | YTVDAIQKKI | TETKQLAKDL | RQWQTNVDVA | NDLALKLLRD |
| YSADDTRKVH | MITENINASW | RSIHKRVSER | EAALEETHRL | LQQFPLDLEK |
| FLAWLTEAET | TANVLQDATR | KERLLEDSKG | VKELMKQWQD | LQGEIEAHTD |
| VYHNLDENSQ | KILRSLEGSD | DAVLLQRRLD | NMNFKWSELR | KKSLNIRSHL |
| EASSDQWKRL | HLSLQELLVW | LQLKDDELSR | QAPIGGDFPA | VQKQNDVHRA |
| FKRELKTKEP | VIMSTLETVR | IFLTEQPLEG | LEKLYQEPRE | LPPEERAQNY |
| TRLLRKQAEE | VNTEWEKLNL | HSADWQRKID | ETLERLQELQ | EATDELDLKL |
| RQAEVIKGSW | QPVGDLLIDS | LQDHLEKVKA | LRGEIAPLKE | NVSHVNDLAR |
| QLTTLGIQLS | PYNLSTLEDL | NTRWKLLQVA | VEDRVRQLHE | AHRDFGPASQ |
| HFLSTSVQGP | WERAISPNKV | PYYINHETQT | TCWDHPKMTE | LYQSLADLNN |
| VRFSAYRTAM | KLRRLQKALC | LDLLSLSAAC | DALDQHNLKQ | NDQPMDILQI |
| INCLTTIYDR | LEQEHNNLVN | VPLCVDMCLN | WLLNVYDTGR | TGRIRVLSFK |
| TGIISLCKAH | LEDKYRYLFK | QVASSTGFCD | QRRLGLLLHD | SIQIPRQLGE |
| VASFGGSNIE | PSVRSCFQFA | NNKPEIEAAL | FLDWMRLEPQ | SMVWLPVLHR |
| VAAAETAKHQ | AKCNICKECP | IIGFRYRSLK | HFNYDICQSC | FFSGRVAKGH |
| KMHYPMVEYC | TPTTSGEDVR | DFAKVLKNKF | RTKRYFAKHP | RMGYLPVQTY |
| LEGDNMETPY | TLINFWPVDS | APASSPQLSH | DDTHSRIEHY | ASRLAEMENS |
| NGSYLNDSIS | PNESIDDEHL | LIQHYCQSLN | QDSPLSQPRS | PAQILISLES |
| EERGELERIL | ADLEEENRNL | QAEYDRLKQQ | HEHKGLSPLP | SPPEMMPTSP |
| QSPRDAELIA | EAKLLRQHKG | RLEARMQILE | DHNKQLESQL | HRLRQLLEQP |
| QAEAKVNGTT | VSSPSTSLQR | SDSSQPMLLR | VVGSQTSDSM | GEEDLLSPPQ |
| DTSTGLEEVM | EQLNNSFPSS | RGRNTPGKPM | REDTM | |

BRIEF DESCRIPTION OF THE DRAWINGS

FIG. 1 shows fluorescence of a normal human muscle slice specimen observed under a fluorescence microscope based on Example 6.

FIG. 2 shows fluorescence of a muscle slice specimen of a human suffering from Duchenne muscular dystrophy observed under a fluorescence microscope in a similar manner as in FIG. 1.

DESCRIPTION OF THE PREFERRED EMBODIMENTS

The peptide containing a part of the amino acid sequence is a peptide shown by, for example, amino acids of at least 10 residues in those of the first to the 3685th in aforesaid amino acid sequence encoded by the gene.

The peptide containing a part of the amino acid sequence is a peptide shown by, for example, amino acids from 10 to 200 residues in those of the first to the 3000th in aforesaid amino acid sequence encoded by the gene.

The peptide containing a part of the amino acid sequence is a peptide shown by, for example, amino acids from 10 to 200 residues in those of the first to the 2000th in aforesaid amino acid sequence encoded by the gene.

The peptide containing a part of the amino acid sequence is a peptide shown by, for example, amino acids from 10 to 200 residues in those of the first to the 1000th in aforesaid amino acid sequence encoded by the gene.

The peptide containing a part of the amino acid sequence is a peptide shown by, for example, amino acids from 10 to 200 residues in those of the first to the 500th in aforesaid amino acid sequence encoded by the gene.

The peptide containing a part of the amino acid sequence is a peptide shown by, for example, amino acids from 10 to 200 residues in those of the 151th to the 350th in aforesaid amino acid sequence encoded by the gene.

The peptide containing a part of the amino acid sequence is a peptide shown by, for example, amino acids from 10 to 100 residues in those of the first to the 3685th in aforesaid amino acid sequence encoded by the gene.

The peptide containing a part of the amino acid sequence is a peptide shown by, for example, amino acids from 10 to 100 residues in those of the first to the 3000th in aforesaid amino acid sequence encoded by the gene.

The peptide containing a part of the amino acid sequence is a peptide shown by, for example, amino acids from 10 to 100 residues in those of the first to the 2000th in aforesaid amino acid sequence encoded by the gene.

The peptide containing a part of the amino acid sequence is a peptide shown by, for example, amino acids from 10 to 100 residues in those of the first to the 1000th in aforesaid amino acid sequence encoded by the gene.

The peptide containing a part of the amino acid sequence is a peptide shown by, for example, amino acids from 10 to 100 residues in those of the first to the 500th in aforesaid amino acid sequence encoded by the gene.

The peptide containing a part of the amino acid sequence is a peptide shown by, for example, amino acids from 10 to 100 residues in those of the 191th to the 290th in aforesaid amino acid sequence encoded by the gene.

The peptide containing a part of the amino acid sequence is a peptide shown by, for example, amino acids from 10 to 60 residues in those of the first to the 3685th in aforesaid amino acid sequence encoded by the gene.

The peptide containing a part of the amino acid sequence is a peptide shown by, for example, amino acids from 10 to 60 residues in those of the first to the 3000th in aforesaid amino acid sequence encoded by the gene.

The peptide containing a part of the amino acid sequence is a peptide shown by, for example, amino acids from 10 to 60 residues in those of the first to the 2000th in aforesaid amino acid sequence encoded by the gene.

The peptide containing a part of the amino acid sequence is a peptide shown by, for example, amino acids from 10 to 60 residues in those of the first to the 1000th in aforesaid amino acid sequence encoded by the gene.

The peptide containing a part of the amino acid sequence is a peptide shown by, for example, amino acids from 10 to 60 residues in those of the first to the 500th in aforesaid amino acid sequence encoded by the gene.

The peptide containing a part of the amino acid sequence is a peptide shown by, for example, amino acids from 10 to 60 residues in those of the 151th to the 350th in aforesaid amino acid sequence encoded by the gene.

The peptide containing a part of the amino acid sequence is a peptide shown by, for example, amino acids from 10 to 60 residues in those of the 190th to the 290th in aforesaid amino acid sequence encoded by the gene.

The peptide containing a part of the amino acid sequence is a peptide shown by, for example, amino acids from 10 to 50 residues in those of the 215th to the 264th in aforesaid amino acid sequence encoded by the gene.

The peptide containing a part of the amino acid sequence is a peptide shown by, for example, amino acids from 20 to 50 residues in those of the 215th to the 264th in aforesaid amino acid sequence encoded by the gene.

The peptide containing a part of the amino acid sequence is a peptide shown by, for example, amino acids from 30 to 50 residues in those of the 215th to the 264th in aforesaid amino acid sequence encoded by the gene.

The peptide containing a part of the amino acid sequence is a peptide shown by, for example, amino acids from 40 to 50 residues in those of the 215th to the 264th in aforesaid amino acid sequence encoded by the gene.

The peptide containing a part of the amino acid sequence is a peptide shown by, for example, amino acids from the 215th to the 264th in aforesaid amino acid sequence encoded by the gene.

The peptide containing a part of the amino acid sequence is a peptide shown by, for example, amino acids from 10 to 200 residues in those of the 201th to the 600th in aforesaid amino acid sequence encoded by the gene.

The peptide containing a part of the amino acid sequence is a peptide shown by, for example, amino acids from 10 to 200 residues in those of the 391th to the 590th in aforesaid amino acid sequence encoded by the gene.

The peptide containing a part of the amino acid sequence is a peptide shown by, for example, amino acids from 10 to 100 residues in those of the 201th to the 600th in aforesaid amino acid sequence encoded by the gene.

The peptide containing a part of the amino acid sequence is a peptide shown by, for example, amino acids from 10 to 100 residues in those of the 301th to the 550th in aforesaid amino acid sequence encoded by the gene.

The peptide containing a part of the amino acid sequence is a peptide shown by, for example, amino acids from 10 to 100 residues in those of the 416th to the 515th in aforesaid amino acid sequence encoded by the gene.

The peptide containing a part of the amino acid sequence is a peptide shown by, for example, amino acids from 10 to 60 residues in those of the 201th to the 600th in aforesaid amino acid sequence encoded by the gene.

The peptide containing a part of the amino acid sequence is a peptide shown by, for example, amino acids from 10 to 60 residues in those of the 301th to the 550th in aforesaid amino acid sequence encoded by the gene.

The peptide containing a part of the amino acid sequence is a peptide shown by, for example, amino acids from 10 to 60 residues in those of the 416th to the 515th in aforesaid amino acid sequence encoded by the gene.

The peptide containing a part of the amino acid sequence is a peptide shown by, for example, amino acids from 10 to 60 residues in those of the 436th to the 495th in aforesaid amino acid sequence encoded by the gene.

The peptide containing a part of the amino acid sequence is a peptide shown by, for example, amino acids from 10 to 50 residues in those of the 440th to the 489th in aforesaid amino acid sequence encoded by the gene.

The peptide containing a part of the amino acid sequence is a peptide shown by, for example, amino acids from 20 to 50 residues in those of the 440th to the 489th in aforesaid amino acid sequence encoded by the gene.

The peptide containing a part of the amino acid sequence is a peptide shown by, for example, amino acids from 30 to 50 residues in those of the 440th to the 489th in aforesaid amino acid sequence encoded by the gene.

The peptide containing a part of the amino acid sequence is a peptide shown by , for example, amino acids from 40 to 50 residues in those of the 440th to the 489th in aforesaid amino acid sequence encoded by the gene.

The peptide containing a part of the amino acid sequence is a peptide shown by, for example, amino acids from the 440th to the 489th in aforesaid amino acid sequence encoded by the gene.

The peptide containing a part of the amino acid sequence is a peptide shown by, for example, amino acids from 10 to 200 residues in those of the 1001th to the 3000th in aforesaid amino acid sequence encoded by the gene.

The peptide containing a part of the amino acid sequence is a peptide shown by, for example, amino acids from 10 to 200 residues in those of the 2001th to the 3000th in aforesaid amino acid sequence encoded by the gene.

The peptide containing a part of the amino acid sequence is a peptide shown by, for example, amino acids from 10 to 200 residues in those of the 2101th to the 2600th in aforesaid amino acid sequence encoded by the gene.

The peptide containing a part of the amino acid sequence is a peptide shown by, for example, amino acids from 10 to 200 residues in those of the 2286th to the 2485th in aforesaid amino acid sequence encoded by the gene.

The peptide containing a part of the amino acid sequence is a peptide shown by, for example, amino acids from 10 to 100 residues in those of the 1001th to the 3000th in aforesaid amino acid sequence encoded by the gene.

The peptide containing a part of the amino acid sequence is a peptide shown by, for example, amino acids from 10 to 100 residues in those of the 2001th to the 3000th in aforesaid amino acid sequence encoded by the gene.

The peptide containing a part of the amino acid sequence is a peptide shown by, for example, amino acids from 10 to 100 residues in those of the 2101th to the 2600th in aforesaid amino acid sequence encoded by the gene.

The peptide containing a part of the amino acid sequence is a peptide shown by, for example, amino acids from 10 to 100 residues in those of the 2335th to the 2434th in aforesaid amino acid sequence encoded by the gene.

The peptide containing a part of the amino acid sequence is a peptide shown by, for example, amino acids from 10 to 60 residues in those of the 1001th to the 3000th in aforesaid amino acid sequence encoded by the gene.

The peptide containing a part of the amino acid sequence is a peptide shown by, for example, amino acids from 10 to 60 residues in those of the 2001th to the 3000th in aforesaid amino acid sequence encoded by the gene.

The peptide containing a part of the amino acid sequence is a peptide shown by, for example, amino acids from 10 to 60 residues in those of the 2101th to the 2600th in aforesaid amino acid sequence encoded by the gene.

The peptide containing a part of the amino acid sequence is a peptide shown by, for example, amino acids from 10 to 60 residues in those of the 2356th to the 2415th in aforesaid amino acid sequence encoded by the gene.

The peptide containing a part of the amino acid sequence is a peptide shown by, for example, amino acids from 10 to 50 residues in those of the 2360th to the 2409th in aforesaid amino acid sequence encoded by the gene.

The peptide containing a part of the amino acid sequence is a peptide shown by, for example, amino acids from 20 to 50 residues in those of the 2360th to the 2409th in aforesaid amino acid sequence encoded by the gene.

The peptide containing a part of the amino acid sequence is a peptide shown by, for example, amino acids from 30 to 50 residues in those of the 2360th to the 2409th in aforesaid amino acid sequence encoded by the gene.

The peptide containing a part of the amino acid sequence is a peptide shown by, for example, amino acids from 40 to 50 residues in those of the 2360th to the 2409th in aforesaid amino acid sequence encoded by the gene.

The peptide containing a part of the amino acid sequence is a peptide shown by, for example, amino acids from the 2360th to the 2409th in aforesaid amino acid sequence encoded by the gene.

The peptide containing a part of the amino acid sequence is a peptide shown by, for example, amino acids from 10 to 200 residues in those of the 1001th to the 3685th in aforesaid amino acid sequence encoded by the gene.

The peptide containing a part of the amino acid sequence is a peptide shown by, for example, amino acids from 10 to 200 residues in those of the 2001th to the 3685th in aforesaid amino acid sequence encoded by the gene.

The peptide containing a part of the amino acid sequence is a peptide shown by, for example, amino acids from 10 to 200 residues in those of the 3001th to the 3685th in aforesaid amino acid sequence encoded by the gene.

The peptide containing a part of the amino acid sequence is a peptide shown by, for example, amino acids from 10 to 200 residues in those of the 3401th to the 3600th in aforesaid amino acid sequence encoded by the gene.

The peptide containing a part of the amino acid sequence is a peptide shown by, for example, amino acids from 10 to 100 residues an those of the 1001th to the 3685th in aforesaid amino acid sequence encoded by the gene.

The peptide containing a part of the amino acid sequence is a peptide shown by, for example, amino acids from 10 to 100 residues an those of the 2001th to the 3685th in aforesaid amino acid sequence encoded by the gene.

The peptide containing a part of the amino acid sequence is a peptide shown by, for example, amino acids from 10 to 100 residues in those of the 3001th to the 3685th in aforesaid amino acid sequence encoded by the gene.

The peptide containing a part of the amino acid sequence is a peptide shown by, for example, amino acids from 10 to 100 residues an those of the 3471th to the 3570th in aforesaid amino acid sequence encoded by the gene.

The peptide containing a part of the amino acid sequence is a peptide shown by, for example, amino acids from 10 to 60 residues in those of the 1001th to the 3685th in aforesaid amino acid sequence encoded by the gene.

The peptide containing a part of the amino acid sequence is a peptide shown by, for example, amino acids from 10 to 60 residues in those of the 2001th to the 3685th in aforesaid amino acid sequence encoded by the gene.

The peptide containing a part of the amino acid sequence is a peptide shown by, for example, amino acids from 10 to 60 residues in those of the 3001th to the 3685th in aforesaid amino acid sequence encoded by the gene.

The peptide containing a part of the amino acid sequence is a peptide shown by, for example, amino acids from 10 to 60 residues in those of the 3401th to the 3600th in aforesaid amino acid sequence encoded by the gene.

The peptide containing a part of the amino acid sequence is a peptide shown by, for example, amino acids from 10 to 60 residues in those of the 3470th to the 3569th in aforesaid amino acid sequence encoded by the gene.

The peptide containing a part of the amino acid sequence is a peptide shown by, for example, amino acids from 10 to 50 residues in those of the 3495th to the 3544th in aforesaid amino acid sequence encoded by the gene.

The peptide containing a part of the amino acid sequence is a peptide shown by, for example, amino acids from 20 to 50 residues in those of the 3495th to the 3544th in aforesaid amino acid sequence encoded by the gene.

The peptide containing a part of the amino acid sequence is a peptide shown by, for example, amino acids from 30 to 50 residues in those of the 3495th to the 3544th in aforesaid amino acid sequence encoded by the gene.

The peptide containing a part of the amino acid sequence is a peptide shown by, for example, amino acids from 40 to 50 residues in those of the 3495th to the 3544th in aforesaid amino acid sequence encoded by the gene.

The peptide containing a part of the amino acid sequence is a peptide shown by, for example, amino acids from the 3495th to the 3544th in aforesaid amino acid sequence encoded by the gene.

The peptide containing a part of the amino acid sequence is a peptide shown by, for example, amino acids from 10 to 200 residues in those of the first to the 200th in aforesaid amino acid sequence encoded by the gene.

The peptide containing a part of the amino acid sequence is a peptide shown by, for example, amino acids from 10 to 100 residues in those of the first to the 200th in aforesaid amino acid sequence encoded by the gene.

The peptide containing a part of the amino acid sequence is a peptide shown by, for example, amino acids from 10 to 100 residues in those of the first to the 100th in aforesaid amino acid sequence encoded by the gene.

The peptide containing a part of the amino acid sequence is a peptide shown by, for example, amino acids from 10 to 60 residues in those of the first the 100th in aforesaid amino acid sequence encoded by the gene.

The peptide containing a part of the amino acid sequence is a peptide shown by, for example, amino acids from 10 to 60 residues in those of the 6th to the 65th in aforesaid amino acid sequence encoded by the gene.

The peptide containing a part of the amino acid sequence is a peptide shown by, for example, amino acids from 10 to 50 residues in those of the 11th to the 60th in aforesaid amino acid sequence encoded by the gene.

The peptide containing a part of the amino acid sequence is a peptide shown by, for example, amino acids from 20 to 50 residues in those of the 11th to the 60th in aforesaid amino acid sequence encoded by the gene.

The peptide containing a part of the amino acid sequence is a peptide shown by, for example, amino acids from 30 to 50 residues in those of the 11th to the 60th in aforesaid amino acid sequence encoded by the gene.

The peptide containing a part of the amino acid sequence is a peptide shown by, for example, amino acids from 40 to 50 residues in those of the 11th to the 60th in aforesaid amino acid sequence encoded by the gene.

The peptide containing a part of the amino acid sequence is a peptide shown by, for example, amino acids from 11th to the 60th in aforesaid amino acid sequence encoded by the gene.

The peptides described above may be peptide derivatives shown by, for example, the general formula:

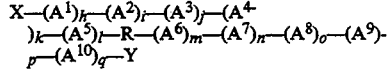

wherein R represents a peptide described above; $A^1$, $A^2$, $A^3$, $A^4$, $A^5$, $A^6$, $A^7$, $A^8$, $A^9$ and $A^{10}$ each represents Ala, Arg, Asn, Asp, Cys, Gln, Glu, Gly, His, Ile, Leu, Lys, Met, Phe, Pro, Ser, Thr, Trp, Tyr or Val; h, i, j, k, l, m, n, o, p and q each represents 0 or 1; X represents a hydrogen atom or an alkyl group, aralkyl group, aryl group or acyl group which may be substituted or unsubstituted; and, Y represents a hydroxy group or an unsubstituted amino group, or an alkylamino group, aralkylamino group or arylamino group which may be substituted or unsubstituted.

The peptides described above may be peptide derivatives shown by, for example, general formula:

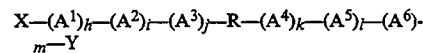

wherein R represents a peptide described above; $A^1$, $A^2$, $A^3$, $A^4$, $A^5$ and $A^6$ each represents Ala, Arg, Asn, Asp, Cys, Gln, Glu, Gly, His, Ile, Leu, Lys, Met, Phe, Pro, Set, Thr, Trp, Tyr or Val; h, i, j, k, 1 or m each represents 0 or 1; X represents a hydrogen atom or an alkyl group, aralkyl group, aryl group or acyl group which may be substituted or unsubstituted; and, Y represents a hydroxy group or an unsubstituted amino group, or an alkylamino group, aralkylamino group or arylamino group which may be substituted or unsubstituted.

The peptides described above may be peptide derivatives shown by, for example, general formula:

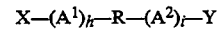

wherein R represents a peptide described above; $A^1$ and $A^2$ each represents Ala, Arg, Asn, Asp, Cys, Gln, Glu, Gly, His, Ile, Leu, Lys, Met, Phe, Pro, Ser, Thr, Trp, Tyr or Val; h and i each represents 0 or 1; X represents a hydrogen atom or an alkyl group, aralkyl group, aryl group or acyl group which may be substituted or unsubstituted; and, Y represents a hydroxy group or an unsubstituted amino group, or an alkylamino group, aralkylamino group or arylamino group which may be substituted or unsubstituted.

The peptides described above may be peptide derivatives shown by, for example, general formula:

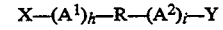

wherein R represents a peptide described above; $A^1$ and $A^2$ each represents Cys or Tyr; h and i each represents 0 or 1; X represents a hydrogen atom or an alkyl group, aralkyl group, aryl group or acyl group which may be substituted or unsubstituted; and, Y represents a hydroxy group or an unsubstituted amino group, or an alkylamino group, aralkylamino group or arylamino group which may be substituted or unsubstituted.

The peptides described above may be peptide derivatives shown by, for example, general formula:

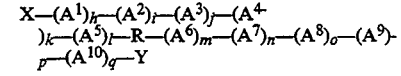

wherein R represents a peptide described above; $A^1$, $A^2$, $A^3$, $A^4$, $A^5$, $A^6$, $A^7$, $A^8$, $A^9$ and $A^{10}$ each represents Ala, Arg, Asn, Asp, Cys, Gln, Glu, Gly, His, Ile, Leu, Lys, Met, Phe, Pro, Set, Thr, Trp, Tyr or Val; h, i, j, k, l, m, n, o, p and q each represents 0 or 1; X represents a hydrogen atom or a lower alkyl group having 1 to 6 carbons atoms, lower aralkyl group having 7 to 13 carbon atoms, aryl group having 6 to 12 carbon atoms or acyl group having 1 to 7 carbon atoms which may be substituted or unsubstituted; and, Y represents a hydroxy group or an unsubstituted amino group, or an alkylamino group having 1 to 6 carbon atoms, aralkylamino group having 7 to 13 carbon atoms or arylamino group having 6 to 12 carbon atoms which may be substituted or unsubstituted.

Herein, when a group is substituted, it means that the group may be substituted by a fluorine atom, a chlorine atom, a bromine atom, an iodine atom, an oxo, a hydroxy group, a $C_1$–$C_6$ alkoxy group, a $C_7$–$C_{13}$ aralkyloxy group, a $C_6$–$C_{12}$ aryloxy group, a $C_1$–$C_6$ aryloxy group, an amino group, a hydroxyamino group, a $C_1$–$C_6$ alkylamino group, a $C_7$–$C_{13}$ aralkylamino group, a $C_6$–$C_{12}$ arylamino group, a $C_1$–$C_6$ arylamino group, a nitro group, a cyano group, an aminosulfonyl group, a carboxy group, a $C_2$–$C_8$ alkyloxycarbonyl group, a $C_8$–$C_{14}$ aralkyloxycarbonyl group, or a $C_7$–$C_{13}$ aryloxycarbonyl group, it may be interrupted by an oxygen atom, a sulfur atom, a nitrogen atom (including one or two hydrogen atoms as appropriate), or a phosphorus atom Preferred substituents are bromine, chlorine, fluorine, oxo, hydroxyl, $C_1$–$C_6$ alkoxy, $C_7$–$C_{13}$ aralkyloxy, carboxy, cyano, or nitro group.

The peptides described above may be peptide derivatives shown by, for example, general formula:

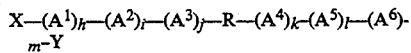

wherein R represents a peptide described above; $A^1$, $A^2$, $A^3$, $A^4$, $A^5$ and $A^6$ each represents Ala, Arg, Asn, Asp, Cys, Gln, Glu, Gly, His, Ile, Leu, Lys, Met, Phe, Pro, Set, Thr, Trp, Tyr or Val; h, i, j, k, l or m each represents 0 or 1; X represents a hydrogen atom or a lower alkyl group having 1 to 6 carbons atoms, lower aralkyl group having 7 to 13 carbon atoms, aryl group having 6 to 12 carbon atoms or acyl group having 1 to 7 carbon atoms which may be substituted or unsubstituted; and, Y represents a hydroxy group or an unsubstituted amino group, or an alkylamino group having 1 to 6 carbon atoms, aralkylamino group having 7 to 13 carbon atoms or arylamino group having 6 to 12 carbon atoms which may be substituted or unsubstituted.

The peptides described above may be peptide derivatives shown by, for example, general formula:

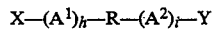

wherein R represents a peptide described above; $A^1$ and $A^2$ each represents Ala, Arg, Asn, Asp, Cys, Gln, Glu, Gly, His, Ile, Leu, Lys, Met, Phe, Pro, Ser, Thr, Trp, Tyr or Val; h and i each represents 0 or 1; X represents a hydrogen atom or a lower alkyl group having 1 to 6 carbons atoms, lower aralkyl group having 7 to 13 carbon atoms, aryl group having 6 to 12 carbon atoms or acyl group having 1 to 7 carbon atoms which may be substituted or unsubstituted; and, Y represents a hydroxy group or an unsubstituted amino group, or an alkylamino group having 1 to 6 carbon atoms, aralkylamino group having 7 to 13 carbon atoms or arylamino group having 6 to 12 carbon atoms which may be substituted or unsubstituted.

The peptides described above may be peptide derivatives shown by, for example, general formula:

wherein R represents a peptide described above; $A^1$ and $A^2$ each represents Cys or Tyr; h and i each represents 0 or 1; X represents a hydrogen atom or a lower alkyl group having 1 to 6 carbons atoms, lower aralkyl group having 7 to 13 carbon atoms, aryl group having 6 to 12 carbon atoms or acyl group having 1 to 7 carbon atoms which may be substituted or unsubstituted; and, Y represents a hydroxy group or an unsubstituted amino group, or an alkylamino group having 1 to 6 carbon atoms, aralkylamino group having 7 to 13 carbon atoms or arylamino group having 6 to 12 carbon atoms which may be substituted or unsubstituted.

To produce these peptides or derivatives thereof, known chemical methods for peptide synthesis can be used; alternatively, biological methods using genes coding for the peptides can be used. The peptides or derivatives thereof may be used to produce antiserum by binding to high molecular weight carriers generally used, for example, bovine serum albumin, thyroglobulin, antitetanic toxoid, Keyhole limpet hemocyanin, etc. by methods conventionally used. The peptides or derivatives thereof are preferably used as they are.

In the methods described above, as the mammals used to produce antiserum there are mammals generally used to produce antiserum, for example, rabbit, goat, rat, mouse, horse, guinea pig, etc.

In the methods described above, to produce antiserum the peptides or derivatives thereof can be administered by an ordinary route, for example, subcutaneously, intramuscularly, intraperitoneally, etc. The peptides or derivatives thereof may be administered alone but preferably together with an adjuvant used to enhance their antibody productivity. As the adjuvant, for example, Freund's complete adjuvant, Freund's incomplete adjuvant, etc. may be used.

As the specimen or sample used for the method described above, a cell slice, a homogenized cell, blood, lymph, etc. may be used. In order to assay the protein in the cell in a simple manner or in order to determine the location of the protein in the cell, however, it is preferred to use a cell slice as the specimen.

For assaying the antigen-antibody complex in the method described above, there are methods generally utilized for assaying an antigen-antibody complex in the immunochemical field. For example, a method which comprises labeling an antiserum or an antibody fraction separated from the antiserum capable of selectively reacting with the objective protein in a specimen with a fluorescent substance, enzyme, radio-isotope, etc. and using the same. In addition to the method using the directly labeled antiserum, or antibody fraction, an antibody (so called second antibody) capable of reacting specifically with the antiserum or antibody fraction, which is labeled with a fluorescent substance, enzyme, radioisotope, etc., may also be used. Upon actual labeling, fluorescein isothiocyanate, etc. can be used as fluorescent label; as enzyme label, peroxidase, alkaline phosphatase, $\beta$-D-galactosidase, etc. can be used; and as the radio-isotope label, $^{125}I$, etc. can be used. The label may be appropriately chosen from these labels and labeling is carried out in a conventional manner in the immunochemical field. For separation of the bound, labeled antigen-antibody complex from the unbound label in an assay for the antigen-antibody complex, any of the separation methods generally utilized in the immunochemical field can be used; for example, any of chromatography, electrophoresis, adsorption, solid phase antibody method and the like can be utilized; these methods can be appropriately chosen based on relation to properties of the specimen and provided for use. Further in case the specimen is immobilized, such as a cell slice, etc., a simple method in which the unbound label is removed by washing to thereby separate the label bound to the antigen-antibody complex on the specimen from the unbound label can be adopted. In this case, any of the methods in which the amount of the label bound to the antigen-antibody complex is directly measured and a method in which the amount of the unbound label is measured thereby to determine the antigen-antibody complex indirectly can be adopted.

Abbreviations and symbols used in the present specification have the following meanings.

| 1 Amino acid residues: | |
|---|---|
| Ala, A: | Alanine |
| Arg, R: | Arginine |
| Asn, N: | Asparagine |
| Asp, D: | Aspartic acid |
| Cys, C: | Cysteine |
| Gln, Q: | Glutamine |
| Glu, E: | Glutamic acid |
| Gly, G: | Glycine |
| His, H: | Histidine |
| Ile, I: | Isoleucine |
| Leu, L: | Leucine |
| Lys, K: | Lysine |
| Met, M: | Methionine |
| Phe, F: | Phenylalanine |
| Pro, P: | Proline |
| Ser, S: | Serine |
| Thr, T: | Threonine |
| Trp, W: | Tryptophane |
| Tyr, Y: | Tyrosine |
| Val, V: | Valine |
| 2. Protecting groups: | |
| Boc | tert-butyloxycarbonyl |
| BrZ | 2-bromobenzyloxycarbonyl |
| Bzl | benzyl |
| ClZ | 2-chlorobenzyloxycarbonyl |
| cHex | cyclohexyl |
| Dnp | 2,4-dinitrophenyl |
| Tos | p-toluenesulfonyl |
| 3. Reagents: | |
| DCC | N,N'-dicyclohexylcarbodiimide |
| DIEA | N,N-diiopropylethylamine |
| DMF | N,N-diethylformamide |
| EDT | 1,2-ethanedithiol |
| HOBT | 1-hydroxybenzotriazole |
| TFA | trifluoroacetic acid |
| 4. Others: | |
| M | molar concentration |
| N | normal concentration |
| Rt | retention time |

Hereafter, the present invention will be described in more detail by referring to the examples but is not contemplated as being limited thereto.

EXAMPLES

Example 1

Using the general method for synthesis of solid phase peptide shown below, the peptide derivatives described in Example 2 and the examples subsequent thereto were synthesized.

As an insoluble resin carrier, 1% divinylbenzene-crosslinked styrene resin (Applied Biosystems Inc.) in which functional groups had been introduced was used.

In each example, amino acids are in the L-form. In condensation, compounds in which amino groups and functional groups on the side chains were protected as shown below were used.

Boc—Ala—OH
Boc—Arg(Tos)—OH
Boc—Asn—OH
Boc—Asp(OcHex)—OH
Boc—Gln—OH
Boc—Gly—OH
Boc—His(Dnp)—OH
Boc—His(Tos)—OH
Boc—Ile—OH
Boc—Leu—OH
Boc—Lys(ClZ)—OH
Boc—Met—OH
Boc—Phe—OH
Boc—Pro—OH
Boc—Ser(Bzl)—OH
Boc—Thr(Bzl)—OH
Boc—Trp(CHO)—OH
Boc—Tyr(BrZ)—OH
Boc—Val—OH

Extension of the peptide chain was carried out by sequentially condensing desired amino acids on the resin by the following procedures.

1. Treating with TFA—CH$_2$Cl$_2$ (1:1) for 90 seconds.
2. Treating with TFA—CH$_2$Cl$_2$ (6:4) for 14 minutes.
3. Washing with CH$_2$Cl$_2$ 3 times.
4. Washing twice with DIEA—DMF (1:9) for 45 seconds.
5. Washing with DMF 6 times.
6. Reacting with the DMF solution of activated amino acids prepared immediately before the reaction for 15 to 30 minutes.
7. Washing with CH$_2$Cl$_2$ 6 times.
8. Monitoring the progress of the reaction by a quantitative ninhydrin monitoring method [Virender K. Satin, Stephen B. H. Kent, James P. Tam and R. B. Merrifield, Anal. Biochem., 117, 147 (1981)] and repeating the procedures of Steps 3 to 7, if the reaction is insufficient.
9. Repeating Steps 1 through 8 in accordance with the desired amino acid sequence.

However, in the condensation of Asn, Gln and Arg, Step 6 was modified as in the following 6'.

6'. Reacting with the DMF solution of activated amino acids prepared immediately before the reaction for 40 minutes to an hour and then washing with DMF twice.

Activation of amino acids were carried out by the following procedures (provided that Asn, Gln and Arg are omitted).

1. Dissolving 2 mmoles of amino acid in 4 ml of CH$_2$Cl$_2$ (in Lys, Pro, His, Leu and Trp, however, a mixture of CH$_2$Cl$_2$-DMF was used).
2. Adding a solution of DCC in CH$_2$Cl$_2$ (concentration of 0.5M, 2 ml) and then reacting for 5 minutes.
3. Adding DMF while evaporating off CH$_2$Cl$_2$ by flowing nitrogen gas into the solution to make a solution of activated amino acid in DMF.

Activation of Ash, Gln and Arg were carried out by the following procedures.

1. Dissolving 2 mmoles of amino acid in 4 ml HOBT in DMF (concentration of 0.5M).
2. Adding a solution of DCC in CH$_2$Cl$_2$ (concentration of 0.5M, 4 ml) and then reacting for 16 minutes.
3. Adding DMF while evaporating off CH$_2$Cl$_2$ by flowing nitrogen gas into the solution to make a solution of activated amino acid in DMF.

Example 2

Tyr-Glu-Lys-Gln-Ser-Asn-Leu-His-Arg-Val-Leu-Met-Asp-Leu-Gln-Asn-Gln-Lys-Leu-Lys-Glu-Leu-Asn-Asp-Trp-Leu-Thr-Lys-Thr-Glu-Glu-Arg-Thr-Arg-

Lys-Met-Glu-Glu-Glu-Pro-Leu-Gly-Pro-Asp-Leu-Glu-Asp-Leu-Lys-Arg-Gln-NH₂

Using as a starting material p-methylbenzhydrylamine hydrochloride resin (0.5 mmoles) obtained by introducing p-methylbenzhydrylamine onto the resin, amino acids were condensed according to the amino acid sequence to thereby extend the peptide chain. Thus the protected peptide-resin (1.39 g) was obtained. As protected His, Boc—His(Tos)—OH was used. In order to examine the condensation yield by the quantitative ninhydrin monitoring method, a part of the resin was withdrawn.

p-Cresol (3 ml) and HF (20 ml) were added to the protected peptide-resin (1.16 g, 0.10.6 mmoles). After reacting at −2° C. for an hour, HF was evaporated off in vacuo. Then, EDT (10 ml) and HF (10 ml) were added to the residue. After reacting at −2° C. for an hour, HF was evaporated off in vacuo. Ether (40 ml) was added to the residue and the mixture was stirred. The supernatant was removed by decantation. This procedure was repeated twice and ether (40 ml) was further added to the residue and the mixture was stirred. Insoluble matters were taken out by filtration, washed with ether and dried to give colorless powder (1.09 g).

To the obtained powder 8M urea aqueous solution (30 ml) was added. After insoluble matters were filtered off, the system was fractionated by reversed phase high performance liquid chromatography (YMC AM-343 (20 mm×250 mm)+GM340-5 (20 mm×50 mm), 0.1% TFA aqueous solution—CH₃CN (25–31% linear gradient (96 minutes)), 10 ml/min, poured separately in 5 portions). The fractions were analyzed by high performance liquid chromatography and the fractions containing the target compound combined with each other. After CH₃CN was evaporated off under reduced pressure, the combined solution was applied to reversed phase high performance liquid chromatography (YMC AM-343 (20 mm×250 mm)+GM340-5 (20 mm×50 mm)) to adsorb and retain on the column. After washing the column with 0.5N acetic acid, elution was performed with 0.5N acetic acid-CH₃CN (4:6). After the CH₃CN was evaporated off under reduced pressure, the residue was lyophilized to give a colorless fluffy powder (110 mg).

Physical properties of the compound obtained
Purity of peptide—98% (based on analysis data by HPLC)
Peptide content—86% (based on amino acid analysis of acid hydrolysate)
Reversed phase high performance liquid chromatography
Rt=25.9 min (YMC AM302 (4.6 mm×150 mm), 0.1% TFA aqueous solution—0.1% TFA solution in CH₃CN (0–50% linear gradient (30 minutes)), 1 ml/min)

| Amino acid anlysis of hydrolysate: | | | | |
|---|---|---|---|---|
| Arg 4.00, | Asp 6.30, | Glu 11.59, | Gly 1.00, | His 1.03, |
| Leu 8.62, | Lys 5.78, | Met 2.02, | Pro 1.83, | Ser 0.94, |
| Thr 2.89, | Tyr 1.09, | Val 0.99, | NH₃ 7.68 | |
| (6N-HCl, 110° C., 24 hours) | | | | |

Mass analysis m/Z=6267 (M+H)

Example 3

Pro-Glu-Asp-Val-Asp-Thr-Thr-Tyr-Pro-Asp-Lys-Lys-Ser-Ile-Leu-Met-Tyr-Ile-Thr-Ser-Leu-Phe-Gln-Val-Leu-Pro-Gln-Gln-Val-Ser-Ile-Glu-Ala-Ile-Gln-Glu-Val-Glu-Met-Leu-Pro-Arg-Pro-Pro-Lys-Val-Thr-Lys-Glu-Glu-NH₂

Using as a starting material p-methylbenzhydrylamine hydrochloride resin (0.5 mmoles) obtained by introducing p-methylbenzhydrylamine onto the resin, amino acids were condensed according to the amino acid sequence to thereby extend the peptide chain. Thus the protected peptide-resin (3.73 g, 76%) was obtained.

Anisole (3 ml) and HF (20 ml) were added to the protected peptide-resin (1.56 g, 0.161 mmoles). After reacting at −2° C. for an hour, HF was evaporated off in vacuo. Ether (40 ml) was added to the residue followed by stirring. The Supernatant was removed by decantation. This procedure was repeated twice and ether (40 ml) was further added to the residue and the mixture was stirred. Insoluble matters were taken out by filtration, washed with ether and dried to give pale yellow powder (1.22 g).

To the obtained powder 8M urea aqueous solution was added. After insoluble matters were filtered off, 29% ammonium hydroxide was added to the system to make 2N ammonium hydroxide solution. The solution was stirred at 0° C. for 30 minutes. TFA was added to render pH 4 and water was added to dilute to 2-fold volume. Urea was added to make 8M urea aqueous solution. Further TFA was added to adjust pH to 2. The mixture was fractionated by reversed phase high performance liquid chromatography (YMC AM-343 (20 mm×250 mm)+GM340-5 (20 mm×50 mm), 0.1% TFA aqueous solution—CH₃CN (38–43% linear gradient (80 minutes)), 10 ml/min, poured separately in 6 portions). The fractions were analyzed by high performance liquid chromatography and the fractions containing the target compound were combined with each other. After CH₃CN was evaporated off under reduced pressure, the combined solution was applied to reversed phase high performance liquid chromatography (YMC AM-343 (20 mm×250 mm)+GM340-5 (20 mm×50 mm)) to adsorb and retain the target compound on the column. After washing the column with 0.5N acetic acid, elution was performed with 0.5N acetic acid—CH₃CN (4:6). After CH₃CN was distilled off under reduced pressure, the residue was lyophilized to give a colorless fluffy powder (158 mg).

Physical properties of the compound obtained
Purity of peptide—99.6% (based on analysis data by HPLC)
Peptide content—83% (based on amino acid analysis of acid hydrolysate)
Reversed phase high performance liquid chromatography
Rt=7.4 min (YMC AM-302 (4.6 mm×150 mm), 0.1% TFA aqueous solution—0.1% TFA solution in CH₃CN (40–60% linear gradient (20 minutes)), 1 ml/min)

| Amino acid analysis of hydrolysate: | | | | |
|---|---|---|---|---|
| Ala 1.00, | Arg 0.95, | Asp 2.90, | Glu 9.75, | Ile 3.40, |
| Leu 3.42, | Lys 3.96, | Met 1.76, | Phe 1.08, | Pro 5.85, |
| Ser 2.64, | Thr 3.66, | Tyr 1.74, | Val 4.52, | NH₃ 4.87 |
| (6N-HCl, 110° C., 24 hours) | | | | |

Mass analysis m/Z=5775 (M+H)

Example 4

Glu-Gly-Pro-Phe-Asp-Val-Gln-Glu-Thr-Glu-Ile-Ala-Val-Gln-Ala-Lys-Gln-Pro-Asp-Val-Glu-Glu-Ile-Leu-Ser-Lys-Gly-Gln-His-Leu-Tyr-Lys-Glu-Lys-Pro-Ala-Thr-Gln-Pro-Val-Lys-Arg-Lys-Leu-Glu-Asp-Leu-Ser-Ser-Glu-NH$_2$

Using as a starting material p-methylbenzhydrylamine hydrochloride resin (0.2 mmoles) obtained by introducing p-methylbenzhydrylamine onto the resin, amino acids were condensed according to the amino acid sequence to thereby extend the peptide chain. Thus the protected peptide-resin (1.54 g, 89%) was obtained. As protected His, Boc—His$_{(Dnp)}$—OH was used.

5% Thiophenol solution in DMF (20 ml) was added to the protected peptide-resin (1.54 g, 0.156 mmoles). After shirring at room temperature for 30 minutes, the reaction mixture was washed with DMF 3 times. Again 5% thiophenol solution in DMF (20 ml) was added to the system. After stirring at room temperature for 30 minutes, the reaction mixture was washed 3 times with DMF and 3 times with DCM followed by drying. Anisole (3 ml) and HF (20 ml) were added to the system. After reacting at −2° C. for an hour, HF was evaporated off in vacuo. Ether (40 ml) was added to the residue and the mixture was stirred. The supernatant was removed by decantation. This procedure was repeated twice and ether (40 ml) was further added to the residue and the mixture was stirred. Insoluble matters were taken out by filtration, washed with ether and dried to give pale yellow powder (1.01 g).

To the obtained powder 8M urea aqueous solution was added. After insoluble matters were filtered off, the system was fractionated by reversed phase high performance liquid chromatography (YMC AM-343 (20 mm×250 mm)+GM340-5 (20 mm×50 mm), 0.1% TFA aqueous solution—CH$_3$CN (24–29% linear gradient (80 minutes)), 10 ml/min, poured separately in 4 portions). The fractions were analyzed by high performance liquid chromatography and the fractions containing the target compound were combined with each other. After CH$_3$CN was evaporated off under reduced pressure, the combined solution was applied to reversed phase high performance liquid chromatography (YMC AM-343 (20 mm×250 mm)+GM340-5 (20 mm×50 mm)) to adsorb and retain the target compound on the column. After washing the column with 0.5N acetic acid, elution was performed with 0.5N acetic acid—CH$_3$CN (4:6). After CH$_3$CN was evaporated off under reduced pressure, the residue was lyophilized to give a colorless fluffy powder (59.3 mg).

Physical properties of the compound obtained
Purity of peptide—97.6% (based on analysis data by HPLC)
Peptide content—75% (based on amino acid analysis of acid hydrolysate)
Reversed phase high performance liquid chromatography
Rt=24.1 min (YMC AM-302 (4.6 mm×150 mm), 0.1% TFA aqueous solution—0.1% TFA solution in CH$_3$CN (0–50% linear gradient (30 minutes)), 1 ml/min)

| Amino acid analysis of hydrolysate: | | | | |
|---|---|---|---|---|
| Ala 3.00, | Arg 0.97, | Asp 2.95, | Glu 12.40, | Gly 2.03, |
| His 1.02, | Ile 1.73, | Leu 3.93, | Lys 5.75, | Phe 1.03, |
| Pro 3.87, | Ser 2.86, | Thr 1.91, | Tyr 0.94, | Val 3.70, |

-continued

| Amino acid analysis of hydrolysate: |
|---|
| NH$_3$ 6.15 |
| (6n-Hcl, 110° C., 24 hours) |

Mass analysis m/z=5664 (M+H)

Example 5

Leu-Ile-Ser-Leu-Glu-Ser-Glu-Glu-Arg-Gly-Glu-Leu-Glu-Arg-Ile-Leu-Ala-Asp-Leu-Glu-Glu-Glu-Asn-Arg-Asn-Leu-Gln-Ala-Glu-Tyr-Asp-Arg-Leu-Lys-Gln-Gln-His-Glu-His-Lys-Gly-Leu-Ser-Pro-Leu-Pro-Ser-Pro-Pro-Glu-NH$_2$

Using as a starting material p-methylbenzhydrylamine hydrochloride resin (0.204 mmoles) obtained by introducing p-methylbenzhydrylamine onto the resin, amino acids were condensed according to the amino acid sequence to thereby extend the peptide chain. Thus the protected peptide-resin (1.54 g, 73%) was obtained. As protected His, Boc—His(Dnp)—OH was used.

5% Thiophenol solution in DMF (20 ml) was added to the protected peptide-resin (1.54 g, 0.149 mmoles). After stirring at room temperature for 30 minutes, the reaction mixture was washed with DMF 3 times. Again 5% thiophenol solution in DMF (20 ml) was added to the system. After stirring at room temperature for 30 minutes, the reaction mixture was washed 3 times with DMF and 3 times with DCM followed by drying. Anisole (3 ml) and HF (20 ml) were added to the system. After reacting at −2° C. for an hour, HF was evaporated off in vacuo. Ether (40 ml) was added to the residue followed by stirring. The supernatant was removed by decantation. This procedure was repeated twice and ether (40 ml) was further added to the residue and the mixture was stirred. Insoluble matters were taken out by filtration, washed with ether and dried to give pale yellow powder (0.992 g).

To the obtained powder 8M urea aqueous solution (about 30 ml) was added. After insoluble matters were filtered off, the system was fractionated by reversed phase high performance liquid chromatography (YMC AM-343 (20 mm×250 mm)+GM340-5 (20 mm×50 mm), 0.1% TFA aqueous solution—CH$_3$CN (28–35% linear gradient (80 minutes)), 10 ml/min, poured separately in 6 portions). The fractions were analyzed by high performance liquid chromatography and the fractions containing the target compound were combined with each other. After CH$_3$CN was evaporated off under reduced pressure, the combined solution was applied to reversed phase high performance liquid chromatography (YMC AM-343 (20 mm×250 mm)+GM340-5 (20 mm×50 mm)) to adsorb and retain on the column. After washing the column with 0.5N acetic acid, elution was performed with 0.5N acetic acid—CH$_3$CN (4:6). After CH$_3$CN was evaporated off under reduced pressure, the residue was lyophilized to give a colorless fluffy powder (51.6 mg).

Physical properties of the compound obtained
Purity of peptide—99.9% (based on analysis data by HPLC)
Peptide content—73% (based on amino acid analysis of acid hydrolysate)
Reversed phase high performance liquid chromatography
Rt=29.4 min (YMC AM-302 (4.6 mm×150 mm), 0.1% TFA aqueous solution−0.1% TFA solution in CH₃CN (0–50% linear gradient (30 minutes)), 1 ml/min)

| Amino acid analysis of hydrolysate: | | | | |
|---|---|---|---|---|
| Ala 2.00, | Arg 3.76, | Asp 4.30, | Glu 13.89, | Gly 2.01, |
| His 1.84, | Ile 1.77, | Leu 9.10, | Lys 2.00, | Pro 3.92, |
| Ser 4.03, | Tyr 0.87, | NH₃ 5.90 | | |
| (6N-HCl, 110° C., 24 hours) | | | | |

Mass analysis m/z=5837 (M+E)

Example 6

After 2 mg of peptide (Tyr-Glu-Lys-Gln-Ser-Asn-Leu-His-Arg-Val-Leu-Met-Asp-Leu-Gln-Asn-Gln-Lys-Leu-Lys-Glu-Leu-Asn-Asp-Trp-Leu-Thr-Lys-Thr-Glu-Glu-Arg-Thr-Arg-Lys-Met-Glu-Glu-Glu-Pro-Leu-Gly-Pro-Asp-Leu-Glu-Asp-Leu-Lys-Arg-Gln-NH₂) was subcutaneously administered to a rabbit (New Zealand white female) together with Freund's complete adjuvant, supplemental immunization wan performed by subcutaneously administering the peptide twice every 2 other weeks together with the same amount of Freund's complete adjuvant. The obtained antiserum was diluted to 800-fold and 30 μl of the dilution and human muscle specimen (sample) having a thickness of 4 μ were incubated at 4° C. for 10 hours. The specimen was then thoroughly washed with cold isotonic phosphate buffer saline (pH 7.4). Then, after reacting with 30 μl of fluorescein isothiocyanate labeled anti-rabbit IgG goat antibody (Tago Co.) at 20° C. for 30 min, the specimen was thoroughly washed with cold isotonic phosphate buffer saline (pH 7.4). Fluorescence of the specimen was measured by a fluorescence microscope (Zeiss, Axiophot). In the case where a normal human muscular slice (cross section) was used as a specimen, fluorescence derived from the antigen-antibody complex was observed on the cell membrane (FIG. 1). In the case where a muscular slice (cross section) of a human suffering from Duchenne muscular dystrophy was used as a specimen, no fluorescence was observed on the cell membrane (FIG. 2).

Example 7

Tyr-Glu-Arg-Glu-Asp-Val-Gln-Lys-Lys-Thr-Phe-Thr-Lys-Trp-Val-Asn-Ala-Gln-Phe-Ser-Lys-Phe-Gly-Lys-Gln-His-Ile-Glu-Asn-Leu-Phe-Ser-Asp-Leu-Gln-Asp-Gly-Arg-Arg-Leu-Leu-Asp-Leu-Leu-Glu-Gly-Leu-Thr-Gly-Gln-NH₂

Using as a starting material p-methylbenzhydrylamine hydrochloride resin (0.284 mmoles) obtained by introducing p-methylbenzhydrylamine onto the resin, amino acids were condensed according to the amino acid sequence to thereby extend the peptide chain. Thus the protected peptide-resin (1.45 g, 50%) was obtained. As protected His, Boc—His(Dnp)—OH was used.

5% Thiophenol in DMF (20 ml) was added to the protected peptide-resin (1.45 g, 0.144 moles). After stirring at room temperature for 30 minutes, the reaction mixture was washed with DMF 3 times. Again 5% thiophenol in DMF (20 ml) was added to the system. After stirring at room temperature for 30 minutes, the reaction mixture was washed 6 times with DMF and 3 times with DCM followed by drying. Anisole (3 ml) and HF (20 ml) were added to the system. After reacting at −2° C. for an hour, HF was evaporated off in vacuo. Then, EDT (10 ml) and HF (10 ml) were added to the residue. After reacting at −2° C. for an hour, HF was evaporated off in vacuo.

Ether (40 ml) was added to the residue and the mixture was stirred. The supernatant was removed by decantation. This procedure was repeated twice and ether (40 ml) was further added to the residue and the mixture was stirred. Insoluble matters were taken out by filtration, washed with ether and dried to give pale yellow powder (1.12 g).

To the obtained powder 1.0M mercaptoethanol in 6M guanidine hydrochloride and 0.05M tris(hydroxymethyl)aminomethane solution (pH 8.0) was added followed by stirring at room temperature for one hour. After insoluble matters were filtered off, the system was fractionated by reversed phase high performance liquid chromatography (YMC AM-343 (20 mm×250 mm)+GM340-5 (20 mm×50 mm), 0.1% aqueous TFA—CH₃CN (33–39% linear gradient (140 minutes)), 10 ml/min, poured separately in 6 portions). The fractions were analyzed by high performance liquid chromatography and the fractions containing the target compound were combined with each other. After CH₃CN was evaporated off under reduced pressure, the combined solution was applied to reversed phase high performance liquid chromatography (YMC AM-343 (20 mm×250 mm)+GM340-5 (20 mm×50 mm)) to adsorb and retain the target compound on the column. After washing the column with 0.5N acetic acid, elution was performed with 0.5N acetic acid—CH₃CN (4:6). After CH₃CN was evaporated off under reduced pressure, the residue was lyophilized to give a colorless fluffy powder (37.5 mg).

Physical properties of the compound obtained

Purity of peptide—95.9% (based on analysis data by HPLC)

Peptide content—78% (based on amino acid analysis of acid hydrolysate)

Reversed phase high performance liquid chromatography

Rt=31.5 min (YMC AM-302 (4.6 mm×150 mm), 0.1% aqueous TFA—0.1% TFA in CH₃CN (0–50% linear gradient (30 minutes)), 1 ml/min)

| Amino acid analysis of hydrolysate: | | | | |
|---|---|---|---|---|
| Ala 1.00, | Arg 2.57, | Asp 5.69, | Glu 8.55, | Gly 3.96, |
| His 0.85 | Ile 0.87, | Leu 6.78, | Lys 4.66, | Phe 3.93, |
| | Ser 1.80, | Thr 2.65, | Tyr 1.07, | Val 1.80, | NH₃8.72, |
| (6N-HCl, 110° C., 24 hours) | | | | |

Mass analysis m/z=5928 (M+H)

Effects of the Invention

As is evident from the foregoing results, according to the method of the present invention, dystrophin which is a protein defective in a human suffering from Duchenne muscular dystrophy can be determined specifically in a simple manner and therefore, the present invention is useful.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A peptide selected from the group consisting of:

(i) Tyr-Glu-Lys-Gln-Ser-Asn-Leu-His-Arg-Val-Leu-Met-Asp-Leu-Gln-Asn-Gln-Lys-Leu-Lys-Glu-Leu-Asn-Asp-Trp-Leu-Thr-Lys-Thr-Glu-Glu-Arg-Thr-Arg-Lys-Met-Glu-Gly-Gly-Pro-Leu-Gly-Pro-Asp-Leu-Glu-Asp-Leu-Lys-Arg-Gln-NH$_2$, (ii) Pro-Glu-Asp-Val-Asp-Thr-Thr-Tyr-Pro-Asp-Lys-Lys-Ser-Ile-Leu-Met-Tyr-Ile-Thr-Ser-Leu-Phe-Gln-Val-Leu-Pro-Gln-Gln-Val-Ser-Ile-Glu-Ala-Ile-Gln-Glu-Val-Glu-Met-Leu-Pro-Arg-Pro-Pro-Lys-Val-Thr-Lys-Glu-Glu-NH$_2$, (iii) Glu-Gly-Pro-Phe-Asp-Val-Gln-Glu-Thr-Glu-Ile-Ala-Val-Gln-Ala-Lys-Gln-Pro-Asp-Val-Glu-Glu-Ile-Leu-Ser-Lys-Gly-Gln-His-Leu-Tyr-Lys-Glu-Lys-Pro-Ala-Thr-Gln-Pro-Val-Lys-Arg-Lys-Leu-Glu-Asp-Leu-Ser-Ser-Glu-NH$_2$, (iv) Leu-Ile-Ser-Leu-Glu-Ser-Glu-Glu-Arg-Gly-Glu-Leu-Glu-Arg-Ile-Leu-Ala-Asp-Leu-Glu-Glu-Glu-Asn-Arg-Asn-Leu-Gln-Ala-Glu-Tyr-Asp-Arg-Leu-Lys-Gln-Gln-His-Glu-His-Lys-Gly-Leu-Ser-Pro-Leu-Pro-Ser-Pro-Pro-Glu-NH$_2$, (v) Tyr-Glu-Arg-Glu-Asp-Val-Gln-Lys-Lys-Thr-Phe-Thr-Lys-Trp-Val-Asn-Ala-Gln-Phe-Ser-Lys-Phe-Gly-Lys-Gln-His-Ile-Glu-Asn-Leu-Phe-Ser-Asp-Leu-Gln-Asp-Gly-Arg-Arg-Leu-Leu-Asp-Leu-Leu-Glu-Gly-Leu-Thr-Gly-Gln-NH$_2$.

2. A method of producing antiserum which specifically reacts with dystrophin, comprising administering a peptide of claim 1 to a mammal, and obtaining said antiserum therefrom.

3. A method of producing an antibody which specifically reacts with dystrophin, comprising administering the peptide of claim 1 to a mammal, obtaining antiserum therefrom, and separating an antibody fraction from said antiserum.

4. A method of producing a monoclonal antibody which specifically reacts with dystrophin, comprising administering the peptide of claim 1 to a mammal, collecting spleen cells therefrom, making fused cells thereof, and cloning said fused cells to produce said antibody.

5. An antiserum which specifically reacts with dystrophin produced by the process of claim 2.

6. An antibody which specifically reacts with dystrophin produced by the process of claim 3.

7. A monoclonal antibody which specifically reacts with dystrophin produced by the process of claim 4.

8. A method for assaying dystrophin, comprising combining the antiserum of claim 5, the antibody of claim 6 or the monoclonal antibody of claim 7 with a specimen or sample to be tested, and measuring or determining the amount of dystrophin-antibody complex formed.

* * * * *